(12) United States Patent
Fukuda et al.

(10) Patent No.: US 6,524,839 B1
(45) Date of Patent: Feb. 25, 2003

(54) METHOD FOR ENHANCING CATALYTIC ACTIVITY OF CELLS

(75) Inventors: Hideki Fukuda, Kobe (JP); Akihiko Kondo, Kobe (JP)

(73) Assignee: Kansai Chemical Engineering Co., Ltd. (JP)

( * ) Notice: Subject to any disclaimer, the term of this patent is extended or adjusted under 35 U.S.C. 154(b) by 0 days.

(21) Appl. No.: 09/744,068

(22) PCT Filed: Jul. 13, 1999

(86) PCT No.: PCT/JP99/03782

§ 371 (c)(1),
(2), (4) Date: Mar. 12, 2001

(87) PCT Pub. No.: WO00/05340

PCT Pub. Date: Feb. 3, 2000

(30) Foreign Application Priority Data

Jul. 21, 1998 (JP) ............................................. 10-205622

(51) Int. Cl.⁷ ............................ C12N 1/38; C12N 1/24; C12N 11/00; C12P 11/00; C12P 7/64
(52) U.S. Cl. ...................... 435/244; 435/251; 435/174; 435/41; 435/130; 435/134
(58) Field of Search ......................... 435/69.1, 174–182, 435/41, 130, 134, 244, 255.1

(56) References Cited

FOREIGN PATENT DOCUMENTS

| JP | 6430584 | 2/1989 | ........... C12N/11/00 |
| JP | 198487 | 4/1989 | ........... C12N/15/00 |
| JP | 297394 | 4/1990 | ........... C12P/13/08 |
| JP | 7231788 | 2/1994 | ........... C12N/15/09 |
| JP | 7227276 | 8/1995 | ............ C12N/1/20 |

OTHER PUBLICATIONS

Liu Y. et al, Production of S–Lactoglutathione by High Activity Whole Cell Biocatalysts Prepared by Permeabilization of Recombinant Saccharomyces cerevisiae with Alcohols, Biotechnology and Bioengeneering, (1999), 64, 54–60.*

Inoue Y. et al, Continuous production of S–lactoylglutatione by immobilized Hansenula mrakii cells, Process. Biochemistry, 1994, 29, 271–275.*

Felix, H., et al. "Permeabilized Cells," Ana. Biochem. 120, 211–234 1982.

Serrano, R., et al. "Assay of Yeast Enzymes *in situ* A Potential Tool in Regulation Studies," Eur. J. Biochem. 34, 479–482 1973.

Gowda, Lalitha R., et al. "Permeabilization of Bakers' yeast by cetyltrimethylammonium bromide for intracellular enzyme catalysis," Enzyme Microb. Technol. 1991, vol. 13, Feb. 154–157.

Seip and Cosimo, "Optimization of Accessible Catalase Activity in Polyacrylamide Gel–Immobilized Saccharomyces cerevisiae," Biotechnol. and Bioeng. vol. 40, 638–642 1992.

Fenton, D. M. "Solvent Treatment for β–D–galactosidase release from yeast cells," Enzyme Microb. Technol. 1982 vol. 4, Jul. 229–232.

Joshi, M. S., et al. "Permeabilization of yeast cells (*Kluyveromyces fragilis*) to lactose by digitonin," Enzyme Microb. Technol. 1989 vol. 11, Jul. 439–443.

Vlach D. "Yeast Cells with High β–Galactosidase Activity and Their Immobilization," J. Mol. Catal. 26 1984 173–185.

Gillespie, E., et al. "Effects of S–lactoylglutathione and inhibitors of glyoxalase on histamine release from human leukocytes," Nature vol. 277 Jan. 11, 1979 135–137.

Kosugi, N., et al. "Production of S–lactoylglutathione by glycerol–adapted *Saccharomyces cerevisiae* and genetically engineered *Escherichia coli* cells," Appl. Microbiol. Biotechnol. 1988 28 263–267.

Thornalley, P.J., et al., "S–D–Lactoylglutathione in Resting and Activated Human Neutrophils," Biochem. Biophys. Res. Commum. vol. 145 No. 2 1987 769–774.

Inoue, Y., and Kimura., A., "Identification of the Structural Gene for Glyoxalase I from *Saccharomyces cerevisiae*," J. Biol. Chem. vol. 271 No. 42 Oct. 18, 1996, 25958–25965.

Inoue, Y., et al. "Production of S–lactoylglutathione by organic–solvent–extracted glyoxalase I from *Hansenula mrakii*," Appl. Microbiol. Biotechnol. 1992 36 469–472.

* cited by examiner

Primary Examiner—Rebecca E. Prouty
Assistant Examiner—Malgorzata A. Walicka
(74) Attorney, Agent, or Firm—Amin & Turocy, LLP

(57) ABSTRACT

Treatment of cells with lower alcohol provides cells having the reaction rate 350 to 600 times higher than that of cells that are not treated with lower alcohol More specifically, a simple operation of treating cells with lower alcohol provides a catalyst that has a higher activity that that of a cell extract and can be recycled.

18 Claims, 1 Drawing Sheet

METHOD FOR ENHANCING CATALYTIC ACTIVITY OF CELLS

FIELD OF THE INVENTION

The present invention relates to a method for producing a desired substance using cells as a catalyst. More specifically, the present invention relates to a method for producing a desired substance using cells treated with lower alcohol as a catalyst.

BACKGROUND OF THE INVENTION

There have been attempts to use cells as a catalyst in biological processes. In order to enhance the catalytic activity of the cells, it is necessary to lower the permeability barrier of cell walls, cell membranes or the like. There have been a large number of reports on attempts to lower the permeability barriers of microorganisms to increase the permeability (Felix et al., Ana. Biochem. 120:211–234 (1982)).

For example, the results of research on enhancing membrane permeability have been reported with respect to yeasts treated with a mixed solution of toluene and ethanol (Serrano Eur. J. Biochem. 34: 479–482 (1973)); cetyltrimethylammonium bromide (Gowda et al., Enzyme Micro. Technol. 13: 154–157 (1991)); ethyl ether (Seip and Cosimo et al., Biotechnol. Bioeng. 40:638–642 (1992)); alcohols (Fenton et al., Enzyme Micro. Technol. 4: 229–232 (1982)); digitonin (Joshi et al., Enzyme Micro. Technol. 11: 439–444 (1989)); Triton X-100 (Vlach et al., J. Mol. Catal. 26:173–185 (1984)); and hexamethylene diamine (Inoue et al., Process biochem. 29: 271–275 (1994)).

However, such research on permeability was conducted for the purpose of determining intracellular enzyme activities in situ and not for the purpose of industrial applications (Felix et al., ibid.).

On the other hand, in recent years, genetic recombination technology has advanced dramatically and excellent gene expression systems have been developed. For example, regarding yeasts, Romanos et al., Yeast 8: 423–488 (1992) describes various gene expression systems. In these gene expression systems, excessive enzymes are produced and accumulated in cells, so that the cells themselves can be an effective catalyst.

Furthermore, for example, if enzymes present in cell cortexes, periplasms or cell membranes, such as lipase which is retained in cell cortices, are used without any treatments or if these enzymes have been expressed by gene manipulation, the cells themselves can be an effective catalyst.

However, in order to utilize the enzymes accumulated in the cells or the enzymes retained in cell cortices, periplasms or cell membranes, it is necessary to lower the barriers of cell walls, cell membranes or the like as described above. However, there is no effective means for lowering the permeability barrier, so that a process of disrupting cells is required. Furthermore, because a process of strict temperature control to prevent inactivation of the enzymes, a purification process, and other processes are required, there are disadvantages that the processes are complicated and lead to high costs.

Therefore, there is a demand for technologies that eliminate disruption of cells, extraction of enzymes and purification, and provide a low-cost catalyst that can be manipulated in a very simple manner, namely, technologies that lower the permeability barrier of cells and use cells themselves as a catalyst.

SUMMARY OF THE INVENTION

The present invention is carried out to solve the above-described problems. The present invention is directed to a cell treated with a lower alcohol, wherein the reaction rate of the treated cell is at least 50 times higher than that of a cell that is not treated with the lower alcohol.

In a preferable embodiment, the cell is yeast or filamentous fungus, and the cell is immobilized onto a carrier.

Furthermore, in a preferable embodiment, the lower alcohol is selected from the group consisting of methanol, ethanol, propanol, and isopropanol.

In a preferable embodiment, the cell is dried.

In a preferable embodiment, the cell contains an enzyme having a resistance to treatment with a lower alcohol.

In a preferable embodiment, the enzyme is glyoxalase I or lipase.

In a preferable embodiment, the enzyme is produced by the expression of a recombinant gene.

In another aspect, the present invention is directed to a catalyst comprising a cell treated with a lower alcohol, wherein the reaction rate of the catalyst is at least 50 times higher than that of a catalyst comprising a cell that is not treated with the lower alcohol.

In a preferable embodiment, the cell is yeast or filamentous fungus.

In another aspect, the present invention is directed to a method for increasing the reaction rate of a cell to at least 50 times higher than that of an untreated cell, comprising treating the cell with a lower alcohol.

In a preferable embodiment, the cell is yeast or filamentous fungus.

In another aspect, the present invention is directed to a method for producing a desired substance by reacting a cell with a substrate, comprising reacting a cell treated with a lower alcohol with the substrate to an enzyme, wherein the reaction rate of the cell treated with the lower alcohol is at least 50 times higher than that of an untreated cell.

In a preferable embodiment, the cell is yeast or filamentous fungus, and preferably the cell is immobilized onto a carrier.

In a preferable embodiment, the cell contains an enzyme having a resistance to treatment with a lower alcohol.

In a preferable embodiment, the enzyme is glyoxalase I, and the desired substance is S-lactoylglutathione.

In a preferable embodiment, the enzyme is lipase and the desired substance is fatty acid ester.

In a preferable embodiment, the glyoxalase I or the lipase is produced by the expression of a recombinant gene.

In a preferable embodiment, the cell is immobilized onto a carrier and filled in a column.

In another aspect, the present invention is directed to a sensor having a cell treated with a lower alcohol, wherein the reaction rate of the treated cell is at least 50 times higher than that of a cell that is not treated with the lower alcohol.

In a preferable embodiment, the cell is yeast or filamentous fungus.

The present invention solves the above-described problems. More specifically, by treating cells with a lower alcohol, the reaction rate of the cells becomes at least 50 times higher than that of untreated cells, and 200 to 600 times higher in preferable cases. This seems to be a result that the treatment with a lower alcohol lowers the permeability barrier of the cell walls or the cell membranes. In the present invention, free cells treated with lower alcohol can be used as a catalyst without any further treatment. Immobilized cells also can be treated with a lower alcohol to be used as a catalyst without any further treatment. The cells or the immobilized cells treated with lower alcohol are further dried for use. Thus, the present invention provides cells having an excellent catalyst activity that can be produced by a very simple method and can be used repeatedly.

Furthermore, the present invention provides a method for producing a desired substance using the cells treated with a lower alcohol as a catalyst.

DETAILED DESCRIPTION OF THE INVENTION

Figure 1:
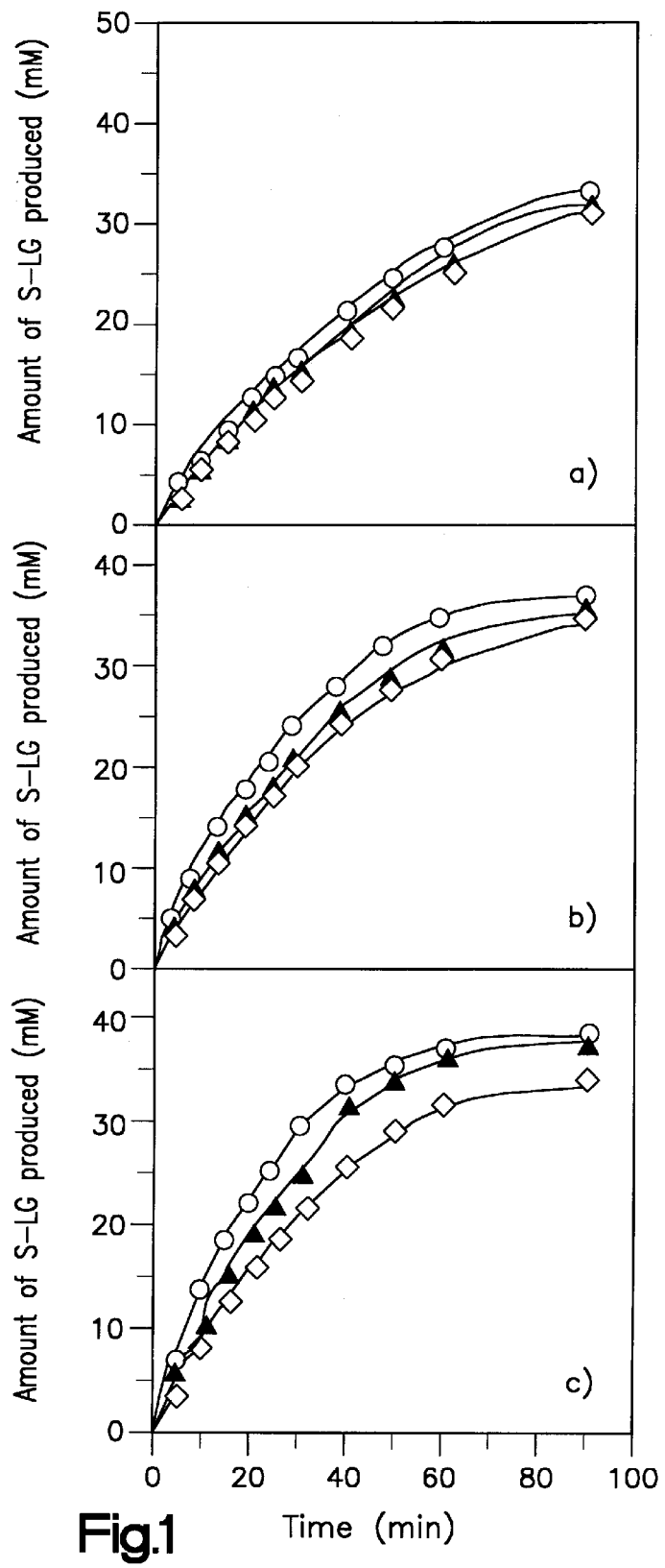
FIGS. 1a to 1c are graphs plotting time versus amount of enzyme produced for yeasts treated with a lower alcohol.

In the present invention, the term "cells" includes Gram-negative bacteria such as *E. coli,* Gram-positive bacteria such as *Bacillus subtilis,* eukaryocyte such as filamentous fungi and yeasts, animal cells, plant cells and the like. in particular, as a host for genetic recombination, *E. coli* that can be used for production of substances, and yeast (for example, yeast belonging to the Saccharomyces genus (*Saccharomyces cerevisiae*), yeast belonging to the Candida genus (*Candida antractica, Candida rugosa,* and *Candida cylindracea*)) are used preferably, but are not limited to these examples. Furthermore, filamentous fungi belonging to the Rhizomucor genus, the Mucor genus, the Aspergillus genus, the Rizopus genus or the Penicillium genus can also be used preferably.

In the present invention, preferable examples of the lower alcohol used for treatment of cells include water-soluble alcohols having a carbon number of 1 to 11. Further, the alcohols can be monovalent, bivalent, or trivalent, and primary alcohols such as methanol and ethanol, secondary alcohols such as isopropanol, and tertiary alcohols such as t-butanol also can be used. Preferably, methanol, ethanol, or isopropanol can be used. The alcohols can be used alone or in combination of two or more.

The concentration of alcohol to treat cells is about 10% to about 100%, preferably about 20% to about 100%, more preferably about 40% to about 80%, and most preferably about 40% to about 60%, although the concentration depends on the alcohol used. When the concentration of alcohol is referred to, V/V % is used.

There is no particular limitation regarding the period of time for alcohol treatment, as long as it is at least 5 minutes. At least 10 minutes is preferable. The treatment period can be changed with the type of alcohol. Although depending on the enzyme, even if a treatment is performed with methanol or ethanol for a long period of time, this hardly affects the enzyme activities, whereas a treatment with isopropanol for a long time tends to reduce the enzyme activities slightly.

There is no particular limitation regarding the temperature of the alcohol treatment, as long as desired enzymes are not inactivated. Therefore, when the enzyme is susceptible to heat, the treatment may be performed at a low temperature. For a heat-resistant enzyme, for example, lipase, the treatment can be performed at a high temperature. For super-thermophilic archaebacteria, the temperature can be as high as 100° C. or more. In general, the temperature is 4° C. to 40° C.

In the present invention, the phrase "enzymes having a resistance to treatment with a lower alcohol" refers to enzymes that are not inactivated (the activities are not lost) by treatment with methanol, ethanol or propanol. Examples of such enzymes include glyoxalase I, lipase, and phospholipase.

In the present invention, the reaction rate can be measured, for example, by using a suitable measuring system, such as measuring the amount of a product or a substrate that has been reduced for a predetermined period of time. The reaction rate referred to in the present invention corresponds to the initial velocity referred to in enzymology.

In the present invention, although cells that have been treated with a lower alcohol may die in many cases, intracellular enzymes are resistant to treatment with the lower alcohol and therefore are not inactivated with treatment with the lower alcohol. In addition, the permeability barriers of cell walls or cell membranes are lowered, so that the cells themselves can be utilized as a catalyst repeatedly. The reaction rate becomes at least 50 times higher, and generally about 100 times higher. When cells are treated under preferable conditions, for example, with about 40% to about 60% of lower alcohol, the activity becomes 300 to 600 times higher.

With regard to recycling the cells as a catalyst, it is preferable that the cells are immobilized onto a carrier. It is preferable that the cells are treated after being immobilized, and the cells may be dried, if necessary. Drying can be performed by any method that does not inactivate the cells, such as vacuum drying and lyophilization.

Immobilization of cells can be performed by any known method such as carrier binding, cross-linking and entrapment. Among these, carrier binding is most preferable in view of handling. Carrier binding includes chemical adsorption by which the cells are adsorbed to an ion-exchange resin, or physical adsorption. In the present invention, physical adsorption using a porous carrier is most preferable. Special means are not required for physical adsorption. Cells and a carrier (for example, a porous body or a foam body) are simply mixed and cultured, so that the cells enter the openings of the carrier and adhere thereto. Thus, immobilized cells can be obtained.

In the present invention, the term "carrier" refers to a substance that can immobilize cells, and preferably a substance that is insoluble in water or a specific solvent. As a material for the carrier used in the present invention, foam bodies or resins, for example, polyvinyl alcohol, polyurethane foam, polystyrene foam, polyacrylamide, polyvinyl formal resin porous body, silicone foam and cellulose porous body, are preferable. A suitable size of openings of the porous bodies or the foam bodies is such that the cells can enter the openings sufficiently and be grown therein, although the size depends on the cells to be immobilized. For bacteria such as *E. coli* or *Bacillus subtilis,* about 10 $\mu$m to about 500 $\mu$m are preferable. For filamentous fungus, yeast, eumycetes and plant cells, 50 $\mu$m to 1,000 $\mu$m are preferable. For animal cells, 30 $\mu$m to 250 $\mu$m are preferable. However, these sizes are only illustrative and do not limit the present invention.

Furthermore, the shape of the carrier can be any shape. In view of the strength of the carrier, the culturing efficiency or the like, spherical or cubical shapes are preferable, and a preferable size is 2 mm to 50 mm in diameter for spherical carriers and 2 mm to 50 mm in length of the side for cubical carriers.

As described above, cell bodies are immobilized in a carrier simply by mixing the cell bodies and the carrier, and can be treated with a lower alcohol without any further processing.

The thus obtained immobilized cells are used for a reaction in a suspension, or can be filled in a column or the like and used as a so-called bioreactor. The cells can be reacted repeatedly in a continuous or batch manner.

The cells (catalyst) of the present invention can be used, not only for production of proteins (enzymes, antibodies, etc.) and amino acids used for pharmaceuticals, foods etc., but also for removal of environmental pollutants. Furthermore, the cells of the present invention also can be used for resolution of optically active substances.

In the present invention, enzymes having a resistance to organic solvent may have been expressed by genetic recombination. It is known to those skilled in the art to introduce a desired gene into a cell to express a desired enzyme (protein). The phrase "introduction of a desired gene" means that a gene is introduced into a cell and expressed. Any method can be used for this operation. This means that, in bacteria, yeast, filamentous fungus, eumycetes, plant or animal cells, a transformant is expressed by inserting the desired gene in the form of plasmid, or by inserting it into a gene of a host, or by effecting homologous recombination with a gene of a host by using transformation, transduction, transfection, cotransfection, electroporation, etc.

The obtained recombinant cell can accumulate a large amount of a desired enzyme (protein) within the cell bodies. Therefore, when the barrier of cell walls or cell membranes is lowered by the method of the present invention so that a substrate is allowed to permeate easily, contact between the substrate and the enzyme is increased so as to obtain the effect of accelerating the enzyme reaction.

The cells or the catalyst of the present invention can be used as a sensor as well. For example, BOD can be measured with oxidation-reduction enzymes in cells. The sensor includes a transducer such as an oxygen electrode and a hydrogen peroxide electrode. The transducer can be determined in view of an enzyme (catalyst) to be used and a substance to be measured. The biosenser of the present invention has the advantages that the permeability of a substrate is good because the permeability barrier is lowered, the sensitivity is high and this biosenser can be used repeatedly.

When the cells used in the present invention produce lipase, the cells are treated with a lower alcohol, and these treated cells can be used as a catalyst for transesterification. Namely, as known to those skilled in the art, when a glycerol ester of fatty acid (e.g., triester) is used as a substrate, and the substrate is reacted with lower alcohol treated cells in the presence of a lower alcohol, a fatty acid ester can be obtained. Fatty acid esters are useful as biodiesel fuel.

Hereinafter, the present invention will be described using the following examples: a process for producing S-lactoylglutathione (which may be referred to as S-LG) from methylglyoxal, using yeast, *Saccharomyces cerevisiae* as a cell and glyoxalase I as an enzyme that is resistant to treatment with a lower alcohol; and production of a fatty acid ester, using filamentous fungus, *Rhizopus oryzae* as a cell and lipase as an enzyme. The present invention is not limited to these examples.

Glyoxalase I catalyzes a reaction from hemimercaptal to S-LG (step B) in the reaction path for producing lactic acid from methylglyoxal, as described below. GSH stands for glutathione.

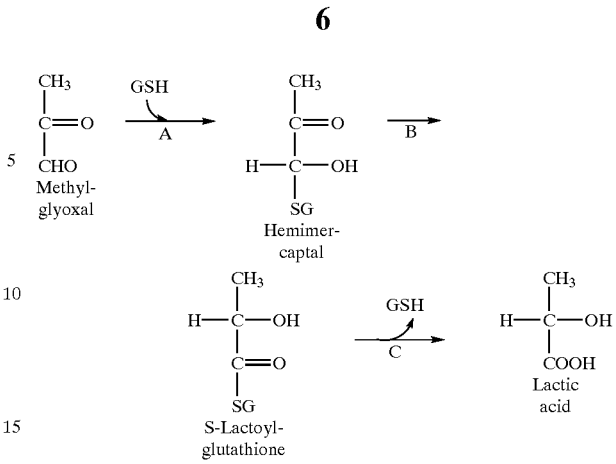

Step A, nonenzymatic; step B, glyoxalase I; step C, glyoxalase II. GSH, glutathione.

S-LG, which is a reaction product, is a compound having several physiological functions (Gillespie et al., Nature 227: 135–136 (1975); Kosugi et al., Appl. Microbiol. Biotechnol. 28: 263–267 (1988); and Thornalley et al., Biochem. Biophys. Res. Commum. 145:769–774 (1979)). There is a demand for the mass production of S-LG for analysis of its physiological functions and applications.

The preparation of yeast that overexpresses glyoxalase I proceeds as follows. Plasmid pE24GLOI having a glyoxalase I gene was donated by Professor Akira Kimura of Research Institute for Food Science, Kyoto University. This plasmid pE24GLOI is a plasmid in which 2500 bp fragment including an open reading frame of glyoxalase I gene (GLOI gene) is incorporated into a multicopy plasmid Yep24 (Ura3), as described by Inoue and Kimura et al., J. Biol. Chem. 271: 25958–25965 (1996). This plasmid pE24GLOI was introduced to yeast, *Saccharomyces cerevisiae* YPH250 (trp⁻, leu⁻, lys⁻, ade⁻, ura3-52), using a lithium acetate method. A transformant was obtained as a strain that grows in agar medium containing SD minimal medium (glucose (20 g/l), Difco yeast nitrogen base w/o amino acids (6.7 g/l)) containing trp, Leu, Lys, and ade in amounts of 40, 60, 30, and 40 µg/ml, respectively.

The obtained transformant was cultured in SD liquid medium having the above-described composition at 30° C. for 16 hours, and a cell extract was obtained by cell extraction method as described below. Then, the activity of glyoxalase I was measured. This transformant (recombinant yeast) accumulated a large amount of glyoxalase I in the cell body, compared with a nontransformant.

The activity of glycoxalase I was determined in the following manner. The cell extract or the treated yeast was suspended in 100 mM phosphate buffer (pH 6.0) containing 50 mM methylglyoxal and 50 mM glutathione and was shaken at 30° C. A predetermined period of time later, an absorbance at 240 nm was measured and an amount of S-LG produced was measured with a molar extinction coefficient of 3300 cm$^{-1}$M$^{-1}$. The production amount (µmol/min/g— wet yeast) per unit time and per unit wet yeast weight was defined as the reaction rate.

EXAMPLE 1-1

The yeast obtained in the above-described manner was precultured in SD minimal medium at 30° C. for 16 hours and then inoculated in fresh SD medium to further culture at 30° C., and the culturing was stopped when OD$_{610}$ of the culture reached 1.0. Yeast cell bodies were collected by centrifugation at 5,000 rpm for 5 minutes. The collected cell pellets were washed with 0.85% NaCl and used for treatments with organic solvents.

Methanol at various concentrations in an amount of 1.0 ml is added to the pellets of the yeast in a wet weight of 0.1 g to suspend the yeast for treatment with organic solvent at 4° C. or 25° C. for a predetermined period of time. After the treatment, treated yeast cell bodies were collected by centrifugation at 5,000 rpm for 5 minutes. The collected cell pellets were washed with 0.85% NaCl and used as an enzyme (catalyst).

EXAMPLE 1-2

The procedure of Example 1-1 is repeated except that ethanol is used in place of methanol.

EXAMPLE 1-3

The procedure of Example 1-1 is repeated except that isopropanol is used in place of methanol.

Comparative Example 1-1

The procedure of Example 1-1 is repeated except that acetone is used in place of methanol.

Comparative Example 1-2

The procedure of Example 1-1 is repeated except that ethyl acetate is used in place of methanol.

Comparative Example 1-3

The procedure of Example 1-1 is repeated except that diethyl ether is used in place of methanol.

Comparative Example 1-4

The procedure of Example 1-1 is repeated except that methanol is not used and 1 ml of 350 mM potassium phosphate buffer at pH 7.0 containing 1% Triton X-100 was added to the pellets of the yeast in a wet weight of 0.1 g to effect a reaction at 4° C. for 10 minutes. After the treatment, the treated yeast cell bodies were collected by centrifugation at 5,000 rpm for 5 minutes. The collected cell pellets were washed with 0.85% NaCl and used as an enzyme (catalyst).

Comparative Example 1-5

The procedure of Example 1-1 is repeated except that methanol is not used and 1 ml of 350 mM potassium phosphate buffer at pH 7.0 containing 1% 80 mM hexamethylene diamine (HMDA) was added to the pellets of the yeast in a wet weight of 0.1 g to effect a reaction at 4° C. for 10 minutes. After the treatment, the treated yeast cell bodies were collected by centrifugation at 5,000 rpm for 5 minutes. The collected cell pellets were washed with 0.85% NaCl and used as an enzyme (catalyst).

Comparative Example 1-6

The procedure of Example 1-1 is repeated except that methanol is not used and the recombinant yeast obtained by culturing and washing was resuspended in 100 mM potassium phosphate buffer at pH 7.0. Yeast calls were disrupted by adding glass beads thereto and by performing 15 cycles of vortexing for 30 seconds and cooling on ice for 1 minute. Then, the cell homogenate was centrifuged at 10,000 g for 20 minutes at 4° C., and a resultant supernatant was used as a cell extract.

Comparative Example 1-7

The procedure of Example 1-1 is repeated except that methanol is not used and a cell extract was prepared by ethyl acetate extraction method based on the method of Inoue et al., Appl. Microbiol. Biotechnol. 36: 469–472 (1992). More specifically, 0.1 g (wet weight) of the recombinant yeast obtained by culturing and washing as described above was resuspended in 2 ml of 100 mM potassium phosphate buffer at pH 7.0, and 2 ml of ethyl acetate was added thereto, followed by incubation at 30° C. for 10 hours and centrifugation at 5,000 rpm for 5 minutes at 4° C. The thus obtained water phase was used as a cell extract.

For all of the examples, the production of S-LG by using the treated yeast is obtained as follows.

The obtained treated yeast in an amount of 0.1 g (wet weight) or an extract from the same amount of cells was suspended in 100 mM phosphate buffer (pH 6.0) containing 50 mM methylglyoxal and 50 mM glutathione (GSH) and was shaken at 30° C. Then, the amount of S-LG produced was measured by the above-described method, and the initial velocity in the production was obtained. Table 1 shows the results of treatments with various concentrations of lower alcohols for various periods of time at 25° C. In Table 1, ND stands for "not done".

TABLE I

| | | Production rate of S-lactoylglutathione ($\mu$mol/min/g-wet weight) | | | | | |
| --- | --- | --- | --- | --- | --- | --- | --- |
| Concentration of organic solvent (%) | Treatment time (min) | Example 1-1 | Example 1-2 | Example 1-3 | Com. Example 1-1 | Com. Example 1-2 | Com. Example 1-3 |
| 0 | 0 | 1.1 | 1.1 | 1.1 | 1.1 | 1.1 | 1.1 |
| 20 | 120 | ND | 18 | 280 | | | |
| | 240 | 18 | 30 | 380 | | | |
| 40 | 10 | 280 | 400 | 550 | | | |
| | 120 | 280 | 368 | 280 | | | |
| | 240 | 260 | 340 | 180 | | | |
| 60 | 10 | 300 | 296 | 296 | | | |
| | 120 | 280 | 188 | 188 | | | |
| | 240 | 280 | 160 | 128 | | | |
| 100 | 10 | 220 | 360 | 398 | 304 | 377 | 337 |
| | 120 | 120 | 360 | 420 | ND | ND | ND |
| | 240 | 100 | 280 | 360 | ND | ND | ND |

Treated at 25° C.

The results of Table 1 show that the lower alcohol treatment drastically increases the reactivity (initial velocity) of the cells by a factor of 200 to 550 (i.e., the permeability barrier of cells was made smaller and the reaction was accelerated), the effects of treating the cells are varied with the type of lower alcohol, and the initial velocity becomes at least 200 times even if the alcohol has a concentration of 40% or more and the treatment is performed for 10 minutes. The results also show that among the lower alcohols, isopropanol can lower the permeability barrier at a relatively lower concentration than methanol and ethanol. These is a tendency that shorter treatment times are better for all the alcohols.

The treatment with diethyl ether, ethyl acetate, or acetone can increase the reactivity of yeast as well as the lower alcohols. However, there is a problem in that a large amount of protein leaks from the cells.

Next, Table 2 shows the results of treating the cells at 4° C. with various concentrations of lower alcohols for various periods of time.

TABLE 2

| Concentration of organic solvent (%) | Treatment time (min) | Production rate of S-lactoylglutathione ($\mu$mol/min/g-wet weight) | | | | | | |
|---|---|---|---|---|---|---|---|---|
| | | Example 1-1 | Example 1-2 | Example 1-3 | Com. Example 1-4 | Com. Example 1-5 | Com. Example 1-6 | Com. Example 1-7 |
| 0 | 0 | 1.1 | 1.1 | 1.1 | 10 | 15 | 109 | 260 |
| 20 | 120 | ND | ND | 10 | | | | |
| | 240 | ND | ND | 10 | | | | |
| 40 | 10 | 180 | 400 | 640 | | | | |
| | 120 | 180 | 340 | 500 | | | | |
| | 240 | 160 | 320 | 300 | | | | |
| 60 | 10 | 340 | 300 | 300 | | | | |
| | 120 | 302 | 387 | 300 | | | | |
| 100 | 10 | 390 | 428 | 460 | | | | |
| | 120 | 345 | 326 | 340 | | | | |

Treated at 4° C.

The results show that although the effects of the treatment at 4° C. are substantially the same as those at 25° C., it is preferable to treat the cells at a lower temperature as the concentration of alcohol is higher, and the treatment at 4° C. has higher effects than at 25° C.

Furthermore, in the treatment with Triton X-100 and the treatment with 80 mM hexamethylene diamine (HMDA), the initial velocity was increased by a factor of 10 to 15, and the treatment with lower alcohols exhibited far larger effects (at least a factor of at least 200).

Furthermore, a liquid obtained by disrupting the yeast with glass beads and extracting, and enzymes extracted with ethyl acetate showed the initial velocity in the reaction of 109 times and 260 times the initial velocity of untreated yeast, respectively. However, the lower alcohol treated yeast of the present invention can be prepared far more easily than these enzyme extracts, and has higher reaction rate. Moreover, the present invention has an advantage in that it can be recycled as shown in Example 2 below.

The yeast cell bodies treated with 40% methanol, ethanol, and propanol at 4° C. for 10 minutes of Examples 1-1, 1-2, and 1-3 were used again to measure the amount of S-LG produced. The results are shown in FIG. 1. FIG. 1a shows the case where yeast was treated with 40% methanol, FIG. 1b shows the case where yeast was treated with 40% ethanol, and FIG. 1c shows the case where yeast was treated with 40% propanol. ○ shows the second use, ▲ shows the third use, and ◇ shows the fourth use. These results show that although the activity is slightly reduced, recycling is possible. These results also suggest that enzymes are retained in the yeast cells treated with lower alcohols, and there is little leakage of enzymes from the cells during catalytic reaction.

EXAMPLE 2-1

First, 100 pieces of polyurethane foams (BSPs) with 6 mm cube as a carrier for immobilization were placed in a shaker flask including 100 ml of lipase production medium (containing 70 g of polypeptone, 1.0 g of $KH_2PO_4$, 1.0 g of $NaNO_3$, 0.5 g of $MgSO_4.7H_2O$ and 20 g of oleic acid in IL), and *Rhizopus oryzae* IFO 4697 was inoculated thereto and cultured at 30° C. for 4 days. The cell bodies were immobilized onto the BSPs during culturing. When the culturing was completed, the BSPs to which the cell bodies were immobilized were collected, and treated with 80% alcohol at 25° C. for 10 minutes. A mixture of soybean oil and methanol in a molar ratio of 1:1 was added thereto, and by utilizing lipase in the treated cell bodies, a reaction for synthesis of fatty acid ester was performed with shaking at 130 times/min at 30° C. for 2 days. The amount of the obtained fatty acid ester was determined by gas chromatography with tricaprilin as the internal standard, using a DB-5 capillary column.

EXAMPLE 2-2

The procedure of Example 2-1 was repeated except that ethanol was used in place of methanol.

EXAMPLE 2-3

The procedure of Example 2-1 was repeated except that isopropanol was used in place of methanol.

Comparative Example 2-1

The procedure of Example 2-1 was repeated except that acetone was used in place of methanol.

Comparative Example 2-2

The procedure of Example 2-1 was repeated except that methanol was not used.

The results of comparing the examples and comparative examples are shown in Table 3.

TABLE 3

| Treatment | Conversion rate (%) |
|---|---|
| Example 2-1 | 9.6 |
| Example 2-2 | 10.0 |
| Example 2-3 | 18.0 |
| Com. Ex. 2-1 | 3.8 |
| Com. Ex. 2-2 | 0.1 |

The results show that the treatment with alcohol, especially the treatment with isopropanol, has a large effect on filamentous fungus as well, and untreated cells have substantially no activity.

The cells treated with a lower alcohol according to the present invention can be used as a catalyst that can be manipulated in a simple manner, have a higher activity by a factor of several hundred compared to untreated cells, and can be recycled. More specifically, by merely treating cells with a lower alcohol, the reaction rate of an enzyme having a resistance to an organic solvent in the cells can reach 600 times higher than that of cells untreated with the lower alcohol. The enzyme activity retained inside the cells, cell cortex, periplasm or the like is expected to increase significantly by lowering the permeability barrier of cell membranes, cell walls or the like.

What is claimed is:

1. A yeast cell treated with a lower alcohol having 1 to 11 carbon atoms at a concentration from about 20 V/V % to about 100 V/V %, the yeast cell comprising an enzyme resistant to inactivation by treatment with the lower alcohol, the enzyme retained in cell cortexes or accumulated in the yeast cell, wherein a reaction rate using the treated yeast cell as a catalyst for a reaction of a substrate from outside the yeast cell is 50 times to 600 times higher than that using a yeast cell comprising the enzyme resistant to inactivation by treatment with the lower alcohol that is not treated with the lower alcohol.

2. The yeast cell of claim 1, wherein the yeast cell is immobilized onto a carrier.

3. The yeast cell of claim 1, wherein the lower alcohol is selected from the group consisting of methanol, ethanol, propanol and isopropanol.

4. The yeast cell of claim 1, wherein the yeast cell is dried.

5. The yeast cell of claim 1, wherein the enzyme is glyoxalase I or lipase.

6. The yeast cell of claim 1, wherein the enzyme is produced by the expression of a recombinant gene encoding the enzyme.

7. A catalyst comprising a yeast cell treated with a lower alcohol having 1 to 11 carbon atoms at a concentration from about 20 V/V % to about 100 V/V %, the yeast cell comprising an enzyme resistant to inactivation by treatment with the lower alcohol, the enzyme retained in cell cortexes or accumulated in the yeast cell, wherein the reaction rate using the catalyst for a reaction of a substrate from outside the yeast cell is 50 times to 600 times higher than that using a catalyst comprising a yeast cell comprising the enzyme resistant to inactivation by treatment with the lower alcohol that is not treated with the lower alcohol.

8. A method for increasing a reaction rate using a yeast cell as catalyst for a reaction of a substrate from outside the yeast cell from 50 times to 600 times higher than that using a yeast cell that is not treated with a lower alcohol having 1 to 11 carbon atoms, comprising treating the yeast cell with the lower alcohol at a concentration from about 20 V/V % to about 100 V/V %, wherein the yeast cell comprises an enzyme resistant to inactivation by treatment with the lower alcohol, the enzyme retained in cell cortexes or accumulated in the yeast cell.

9. A method for producing a desired substance by using a substrate and a yeast cell as a catalyst, comprising reacting the yeast cell treated with lower alcohol having 1 to 11 carbon atoms at a concentration from about 20 V/V % to about 100 V/V % with the substrate, wherein the reaction rate using the yeast cell is 50 times to 600 times higher than that using an untreated yeast cell, and the yeast cell contains an enzyme resistant to inactivation by treatment with the lower alcohol, the enzyme retained in cell cortexes or accumulated in the yeast cell.

10. The method of claim 9, wherein the enzyme is glyoxalase I and the desired substance is S-lactoylglutathione.

11. The method of claim 9, wherein the enzyme is lipase and the desired substance is a fatty acid ester.

12. The method of claim 10, wherein the enzyme is produced by the expression of a recombinant gene encoding the enzyme.

13. The method of claim 10, wherein the yeast cell is immobilized onto a carrier and fills in a column.

14. The yeast cell of claim 3, wherein the yeast cell is dried.

15. The yeast cell of claim 5, wherein the enzyme is produced by the expression of a recombinant gene encoding the enzyme.

16. The method of claim 11, wherein the enzyme is produced by the expression of a recombinant gene encoding the enzyme.

17. The method of claim 11, wherein the yeast cell is immobilized onto a carrier and fills in a column.

18. The method of claim 12, wherein the yeast cell is immobilized onto a carrier and fills in a column.

* * * * *